US011976098B2

(12) United States Patent
Shen et al.

(10) Patent No.: US 11,976,098 B2
(45) Date of Patent: May 7, 2024

(54) COOKED MILLET PROLAMIN PEPTIDE FOR INHIBITING ALPHA-AMYLASE AND ALPHA-GLUCOSIDASE

(71) Applicant: China Agricultural University, Beijing (CN)

(72) Inventors: Qun Shen, Beijing (CN); Qingyu Zhao, Beijing (CN); Chao Wang, Beijing (CN); Yong Xue, Beijing (CN)

(73) Assignee: CHINA AGRICULTURAL UNIVERSITY, Beijing (CN)

(*) Notice: Subject to any disclaimer, the term of this patent is extended or adjusted under 35 U.S.C. 154(b) by 0 days.

(21) Appl. No.: 18/116,331

(22) Filed: Mar. 2, 2023

(65) Prior Publication Data

US 2023/0331791 A1 Oct. 19, 2023

(30) Foreign Application Priority Data

Apr. 15, 2022 (CN) ......................... 202210396241.7

(51) Int. Cl.

| | |
|---|---|
| ***C07K 14/415*** | (2006.01) |
| ***A23L 33/00*** | (2016.01) |
| ***A23L 33/18*** | (2016.01) |
| ***A61K 38/00*** | (2006.01) |

(52) U.S. Cl.

CPC ............ *C07K 14/415* (2013.01); *A23L 33/18* (2016.08); *A23L 33/40* (2016.08); *A61K 38/00* (2013.01)

(58) Field of Classification Search

CPC ....... C07K 14/415; A23L 33/18; A23L 33/40; A61K 38/00

See application file for complete search history.

(56) References Cited

U.S. PATENT DOCUMENTS

| | | | | |
|---|---|---|---|---|
| 2007/0083334 A1* | 4/2007 | Mintz | G16B 40/00 702/19 |
| 2018/0104303 A1 | 4/2018 | La Rochelle et al. | |

FOREIGN PATENT DOCUMENTS

| | | | |
|---|---|---|---|
| CN | 111154823 A | 5/2020 | |
| CN | 113025678 A | 6/2021 | |
| CN | 114106128 A | 3/2022 | |
| CN | 113336825 B | 4/2022 | |
| CN | 114716524 A | 7/2022 | |
| IN | 114716523 A | 7/2022 | |
| WO | WO 2020/072700 * | 4/2020 | A61K 35/15 |

OTHER PUBLICATIONS

Zhongwei Ji, Study on the Preparation of Foxtail Millet Prolamins Peptide and Its Antioxidant and Anti-inflammatory Activities, 2020, pp. 7-8.

* cited by examiner

*Primary Examiner* — Amber D Steele
(74) *Attorney, Agent, or Firm* — Bayramoglu Law Offices LLC

(57) ABSTRACT

A cooked millet prolamin peptide for inhibiting α-amylase and α-glucosidase, an application thereof, and a screening method thereof are disclosed. The sequence of the peptide is selected from SEQ ID NOS: 1-6. The peptide provided in the present disclosure can effectively inhibit the activities of α-glucosidase and α-amylase simultaneously and is safe and non-toxic and has no side effects. Therefore, the peptide has a good potential and application prospect as a functional component in food, health products, and hypoglycemic drugs.

3 Claims, 8 Drawing Sheets

Specification includes a Sequence Listing.

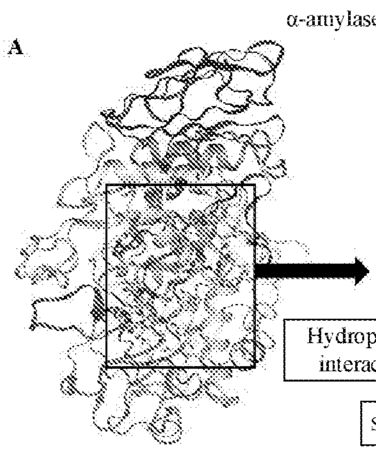
FIG. 5A
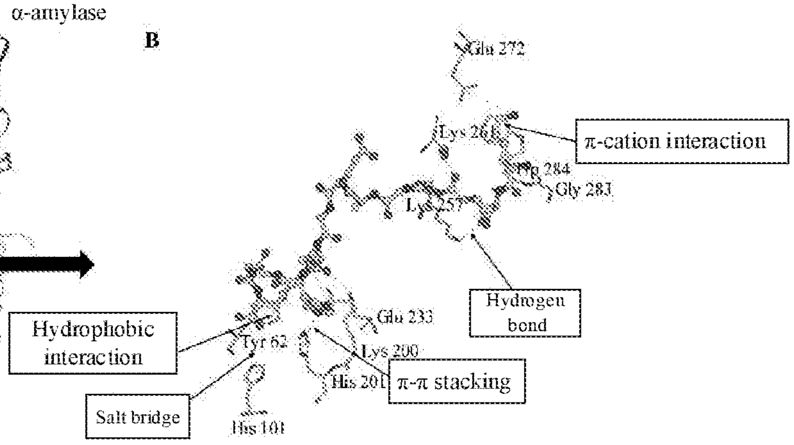
FIG. 5B
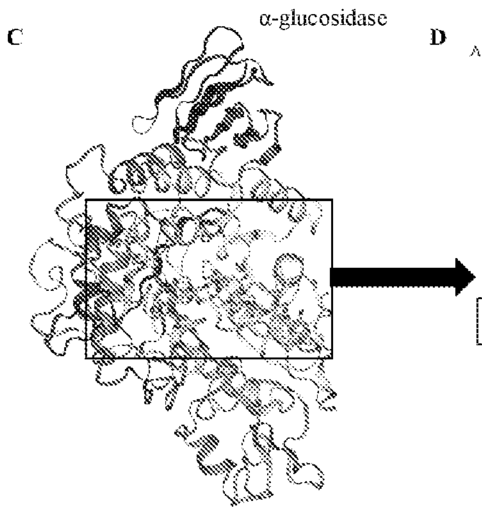
FIG. 5C
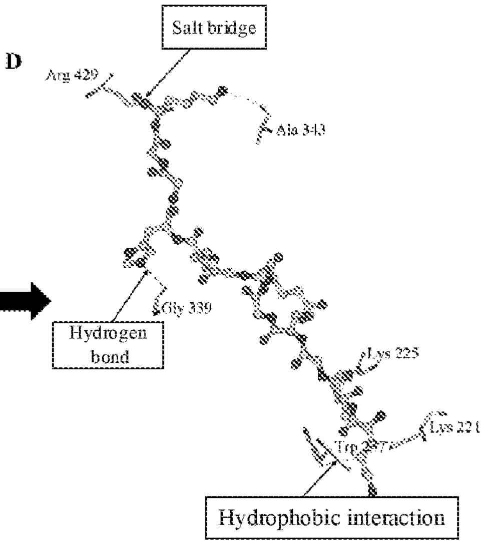
FIG. 5D
FIG. 5

COOKED MILLET PROLAMIN PEPTIDE FOR INHIBITING ALPHA-AMYLASE AND ALPHA-GLUCOSIDASE

CROSS REFERENCE TO THE RELATED APPLICATIONS

This application is based upon and claims priority to Chinese Patent Application No. 202210396241.7, filed on Apr. 15, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBNYDX001-PKG_Sequence_Listing.xml, created on Jan. 31, 2023, and is 33,330 bytes in size.

TECHNICAL FIELD

The present disclosure belongs to the field of proteins. Specifically, the present disclosure provides a plurality of cooked millet prolamin peptides for inhibiting α-amylase and α-glucosidase, an application thereof, and a screening method thereof.

BACKGROUND

Diabetes has become a globally prevalent metabolic disease and is mainly manifested by metabolic disorders of body fat, carbohydrates, and proteins caused by increased blood glucose levels. The prevalence of diabetes has been steadily increasing in recent years. Non-insulin-dependent diabetes, i.e., type 2 diabetes, is common in people of all ages, and 90% of patients with diabetes have been diagnosed with type 2 diabetes. Dietary starch can be digested by α-amylase to produce a large amount of maltose which is then digested by α-glucosidase to form glucose. Elevated blood glucose levels caused by the rapid degradation of starch into glucose are referred to as postprandial hyperglycemia, which is an essential indicator of type 2 diabetes. Therefore, postprandial blood glucose can be controlled by inhibiting α-amylase and α-glucosidase to reduce the rate of carbohydrate hydrolysis to glucose. Currently available drugs for treating type 2 diabetes, such as metformin, acarbose, voglibose, and miglitol, can inhibit the activities of α-amylase and α-glucosidase, but the intake of these hypoglycemic drugs also has some side effects, such as flatulence and diarrhea.

In recent years, many foodborne peptides have been proven to have antibacterial properties, functions of lowering blood pressure and cholesterol, and antithrombotic and antioxidant activities. Food proteins have received much attention as a major source of functional peptides. Millet prolamin has been proven to have a good function in improving blood glucose metabolism. In other words, after millet prolamin is intragastrically administrated to diabetic mice, the millet prolamin is digested in the gastrointestinal tract and hydrolyzed to amino acids and peptides which enter the blood circulation to play physiological roles such as lowering blood glucose levels. Presently, the peptides for antioxidant, anti-inflammatory, and lipase inhibition have been isolated from millet prolamin, but there is a lack of research on millet prolamin hypoglycemic peptides. Therefore, it is necessary to explore peptide fragments in the small-molecular peptides obtained from the hydrolysis of millet prolamin which can be used as potential functional hypoglycemic substances.

SUMMARY

Given the above problems, in one aspect, the present disclosure provides a cooked millet prolamin peptide for inhibiting α-amylase and α-glucosidase. The sequence of the peptide is selected from SEQ ID NOS: 1-6.

Further, the sequence of the peptide is shown in SEQ ID NO: 1 or SEQ ID NO: 2.

In another aspect, the present disclosure provides a composition, and the composition includes the peptide described above and an acceptable excipient for pharmaceutical, food, or health products.

In another aspect, the present disclosure provides a use of the peptide or the composition described above in the preparation of α-amylase and/or α-glucosidase inhibitors.

In another aspect, the present disclosure provides an application of the peptide or the composition described above in the preparation of drugs for the treatment of diabetes.

In another aspect, the present disclosure provides an application of the peptide or the composition described above in the preparation of hypoglycemic food or health products suitable for diabetic populations.

Further, the diabetes is type 2 diabetes.

In another aspect, the present disclosure provides a method for screening the peptide, and the method includes:

(1) in vitro simulated digestion: hydrolyzing cooked millet prolamin by enzymolysis to obtain protein hydrolysate;

(2) screening: conducting an ultrafiltration process of the protein hydrolysate, performing a mass spectrometry sequencing to obtain the peptide fragment sequences with high confidence coefficient from an ultrafiltration grade component, carrying out a virtual screening of the peptide fragment sequences by Dock 6.9 software, screening peptide fragments with good docking effects with α-glucosidase and α-amylase, respectively, according to the grid score and the internal repulsion energy of the peptide fragments, and comparing the peptide fragments with good docking effect with α-glucosidase and the peptide fragments with good docking effect with α-amylase to obtain the peptide fragments with good docking effects with both α-glucosidase and α-amylase;

(3) active site analysis and in vitro function prediction: docking the peptide sequences obtained by screening in prior paragraph with α-amylase and α-glucosidase, respectively, by Dock 6.9 software to determine the key amino acids and interaction forces between the peptide sequences and α-amylase and α-glucosidase, and conducting a prediction of the properties, such as water solubility, instability, isoelectric point, half-life period, and ADMET (Absorption, Distribution, Metabolism, Elimination and Toxicity), of the screened peptide sequences with good docking effects with both α-glucosidase and α-amylase.

Further, pepsin and pancreatin enzyme are used in hydrolysis.

Further, the ultrafiltration grade component is less than 3 kDa.

Advantages:

In the present disclosure, six small peptides unreported before, namely, QQLRPF shown in SEQ ID NO: 1, AGAGPQGRP shown in SEQ ID NO: 2, FALQGAAFLGSA shown in SEQ ID NO: 3, QQQQLLR shown in SEQ ID NO: 4, KTGSGAEGMHGGK shown in SEQ ID NO: 5, and KAHAALGAK shown in SEQ ID NO: 6, were screened from cooked millet prolamin for the first time, which can effectively inhibit the activities of α-glucosidase and α-amylase simultaneously. The structures of the small peptides SEQ ID NO: 1, SEQ ID NO: 2, SEQ ID NO: 3, SEQ ID NO: 4 SEQ ID NO: 5 and SEQ ID NO: 6 were also defined. At the same time, the six small peptides SEQ ID NO: 1, SEQ ID NO. 2, SEQ ID NO: 3, SEQ ID NO: 4, SEQ ID NO: 5, and SEQ ID NO: 6 have the advantages of safety, non-toxicity, and no side effects. Therefore, the peptides have a good potential and application prospect as a functional component in food, health products, and hypoglycemic drugs.

BRIEF DESCRIPTION OF THE DRAWINGS

FIGS. 5A-5D show the docking result of KTGSGAEGMHGGK, shown in SEQ ID NO: 5, with α-glucosidase and the docking result of SEQ ID NO: 5 with α-amylase.

DETAILED DESCRIPTION OF THE EMBODIMENTS

Figure 1A:
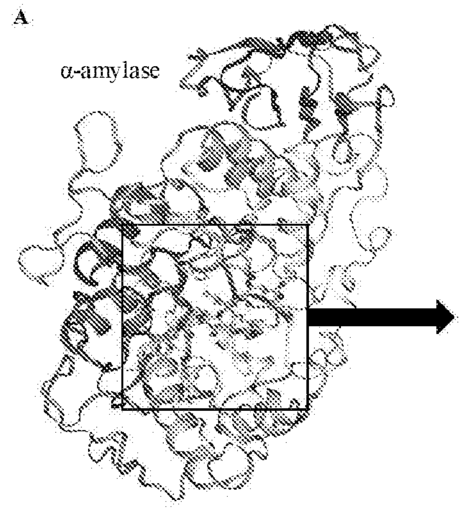
FIGS. 1A-1D show the docking result of QQLRPF, shown in SEQ ID NO: 1, with α-glucosidase and the docking result of SEQ ID NO: 1 with α-amylase.

Embodiment 1: Extraction of Cooked Millet Prolamin

The millet was first ground into powder and sifted through a 60-mesh sieve. The resulting millet powder was dispersed in n-hexane at a ratio of 1:5 (w/v), followed by shaking in a water bath at 37° C. for 4 h and allowing the solution to stand. After the resulting millet powder and the n-hexane were stratified, the upper layer of n-hexane was discarded, and the lower layer of precipitate was collected and dried in a fume hood for 24 h to completely remove the n-hexane to obtain raw millet powder. The degreased raw millet powder and distilled water were mixed evenly at a ratio of 1:5 (w/v) and gelatinized for 10 min in a boiling water bath. The resulting precipitate was dried in an oven at 43° C. for 24 h and then powdered and sifted through a 60-mesh sieve to obtain cooked millet powder. The cooked millet powder was dispersed in a 70% ethanol solution at a ratio of 1:7 (m/v), followed by shaking in a water bath oscillator at 40° C. for 2 h. The resulting reaction solution was centrifuged at 7000 rpm for 10 min, and the resulting supernatant was collected and dialyzed in a dialysis bag for 24 h. The distilled water was replaced 4 times during dialysis. After dialysis, the resulting dialysate was centrifuged at 7000 rpm for 5 min, and the resulting precipitate was collected and lyophilized to obtain the cooked millet prolamin with a protein content of 85%.

Embodiment 2: In Vitro Simulated Digestion of Cooked Millet Prolamin

The cooked millet prolamin sample was mixed with distilled water at a ratio of 1:5 (w/v), the pH was adjusted to 3, and 2000 U/mL of pepsin was added. After reacting for 2 h, the pH was adjusted to 7. Pancreatin enzyme was added at a concentration of 100 U trypsin per 1 mL of digestive fluid. The reaction was continued for 2 h. After the reaction was over, the enzyme was deactivated in a boiling water bath for 10 min to terminate the reaction. Finally, the precipitate was collected by centrifugation at 7000 rpm for 10 min to obtain the hydrolysate of digested protein.

Embodiment 3: Ultrafiltration of the In Vitro Simulated Digestion Products of Cooked Millet Prolamin First, an Amicon® Ultra-15 centrifugal filter was pre-cleaned with ultra-pure water and dried after pre-cleaning. The centrifugal filter with a separation molecular weight of 3 kDa was selected and added with a sample of no more than 15 mL. The filter device covered with a lid was put into a centrifugal rotor for rotation for about 30 min at a rotational speed of 5000×g. After centrifugation, the lid and filter were removed, and the liquid in the centrifuge tube was collected and lyophilized to obtain the protein hydrolysate ultrafiltration sample less than 3 kDa.

Embodiment 4: Mass Spectrometry Sequencing and Screening of the In Vitro Simulated Digestion Products of Cooked Millet Prolamin The components of the hydrolysate less than 3 kDa were subjected to mass spectrometry sequencing by an electrospray-combined ion trap Orbitrap mass spectrometer, and the peptide sequences were analyzed by a de novo method to obtain all the peptide sequences with high confidence coefficient. Then, the peptides obtained by sequencing, based on the grid score of less than −115 kcal/mol and the internal repulsion energy of less than 30 kcal/mol, were virtually screened with α-glucosidase and α-amylase, respectively, by Dock 6.9 software. The screening results are shown in Table 1 and Table 2. Comparing Table 1 and Table 2, it can be found that small peptides QQLRPF shown in SEQ ID NO: 1, AGAGPQGRP shown in SEQ ID NO: 2, FALQGAAFLGSA shown in SEQ ID NO: 3, QQQQLLR shown in SEQ ID NO: 4, KTGSGAEGMHGGK shown in SEQ ID NO: 5, and KAHAALGAK shown in SEQ ID NO: 6 have better docking effects with both α-glucosidase and α-amylase.

TABLE 1

Peptides with good docking effect with α-amylase in virtual screening

| SEQ ID NO: | Sequence | Grid score (kcal/mol) | Van der Waals force (kcal/mol) | Electrostatic force (kcal/mol) | Internal repulsion energy (kcal/mol) |
|---|---|---|---|---|---|
| 5 | KTGSGAEG MHGGK | -152.065 | -121.745 | -30.3203 | 29.821 |
| 7 | TLFDGHAA LGAK | -148.936 | -126.699 | -22.2371 | 29.4055 |
| 8 | TSGAAGN GVDAFGQ | -143.316 | -135.542 | -7.7739 | 26.7281 |
| 3 | FALQGAAF LGSA | -136.847 | -123.049 | -13.7978 | 29.7369 |
| 9 | THVKKQQ | -128.936 | -103.875 | -25.0614 | 28.0828 |
| 6 | KAHAALG AK | -128.263 | -104.742 | -23.5212 | 27.4757 |
| 4 | QQQQLLR | -121.389 | -99.6055 | -21.7838 | 25.4738 |
| 1 | QQLRPF | -121.306 | -101.535 | -19.7709 | 27.2623 |
| 2 | AGAGPQG RP | -117.658 | -96.1684 | -21.4899 | 22.6545 |
| 10 | FQQFRP | -116.577 | -96.8112 | -19.7656 | 20.0226 |
| 11 | QQLLLPW | -115.605 | -96.7665 | -18.8383 | 25.6813 |

TABLE 2

Peptides with good docking effect with α-glucosidase in virtual screening

| SEQ ID NO: | Sequence | Grid score (kcal/mol) | Van der Waals force (kcal/mol) | Electrostatic force (kcal/mol) | Internal repulsion energy (kcal/mol) |
|---|---|---|---|---|---|
| 3 | FALQGAAFL GSA | -155.651 | -144.458 | -11.1934 | 27.7357 |
| 5 | KTGSGAEG MHGGK | -152.479 | -133.221 | -19.258 | 28.0528 |
| 12 | GPAGHVKN Q | -150.991 | -127.832 | -23.1587 | 29.119 |
| 13 | TMAALGAK | -149.691 | -117.439 | -32.2518 | 28.3463 |
| 6 | KAHAALGA K | -143.263 | -106.148 | -37.1147 | 23.8761 |
| 14 | QGGPAGGR P | -141.531 | -133.419 | -8.1117 | 19.6846 |
| 15 | GPAGPQGPR | -136.794 | -105.012 | -31.7815 | 24.5535 |
| 16 | PSLVRGPR | -133.187 | -107.608 | -25.5786 | 28.0496 |
| 2 | AGAGPQGR P | -130.089 | -100.711 | -29.3784 | 29.2749 |
| 17 | AGPAGRP | -122.886 | -100.843 | -22.0428 | 21.737 |
| 18 | TNRFKP | -122.602 | -96.4056 | -26.1962 | 23.5706 |
| 19 | QQLLAPW | -121.941 | -118.523 | -3.4175 | 29.6769 |
| 20 | FTSSKPF | -121.645 | -97.7482 | -23.8968 | 29.2416 |
| 1 | QQLRPF | -121.178 | -106.425 | -14.7534 | 23.4919 |

TABLE 2-continued

| Peptides with good docking effect with α-glucosidase in virtual screening | | | | | |
|---|---|---|---|---|---|
| SEQ ID NO: | Sequence | Grid score (kcal/mol) | Van der Waals force (kcal/mol) | Electrostatic force (kcal/mol) | Internal repulsion energy (kcal/mol) |
| 21 | THEGQMSP | -120.728 | -110.295 | -10.4326 | 23.9988 |
| 22 | FSWTPR | -120.695 | -105.678 | -15.0169 | 24.4493 |
| 23 | YGVTHPCG | -120.033 | -105.671 | -14.3625 | 22.4862 |
| 24 | YAMTPR | -119.305 | -91.846 | -27.4588 | 27.7076 |
| 4 | QQQQLLR | -119.111 | -95.3296 | -23.781 | 24.5052 |
| 25 | FYWTPR | -118.513 | -105.079 | -13.4341 | 28.163 |
| 26 | QQFYPF | -115.064 | -107.588 | -7.4758 | 26.6875 |

Figure 1B:
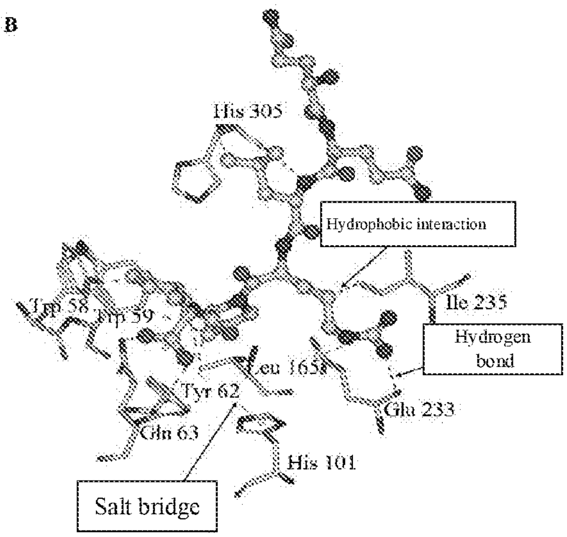
Figure 1C:
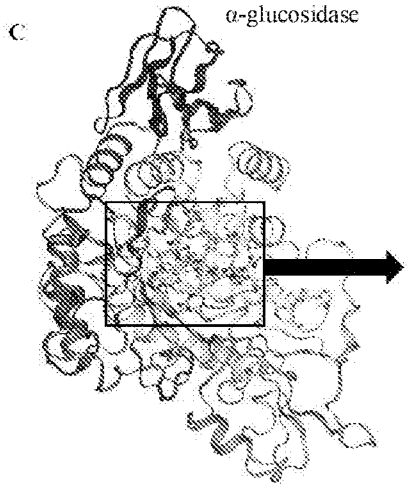
Figure 1D:
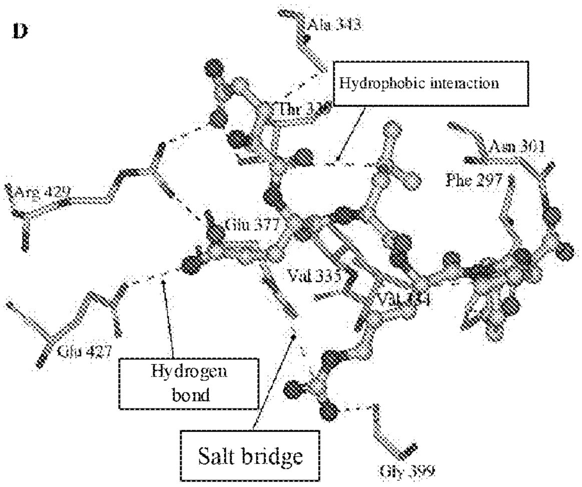
Figure 2A:
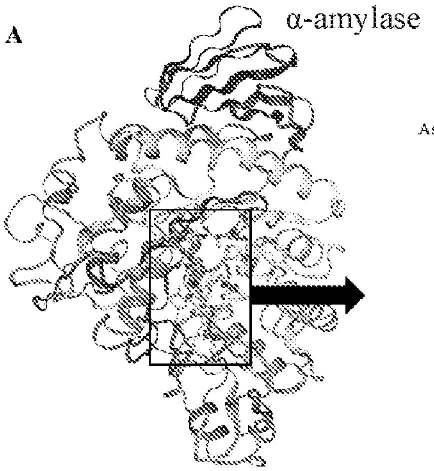
FIGS. 2A-2D show the docking result of AGAGPQGRP shown in SEQ ID NO: 2, with α-glucosidase and the docking result of SEQ ID NO: 2 with α-amylase.
Figure 2B:
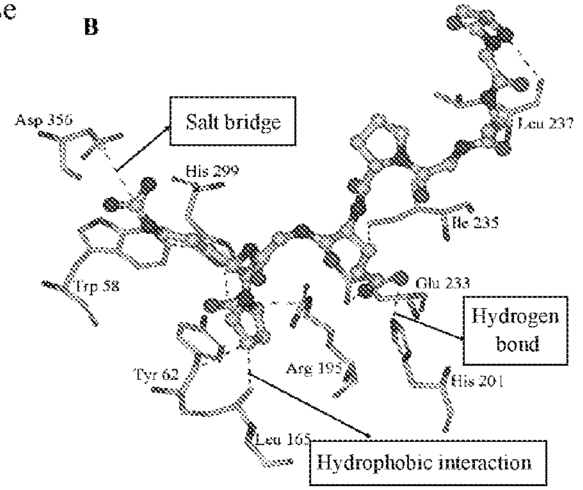
Figure 2C:
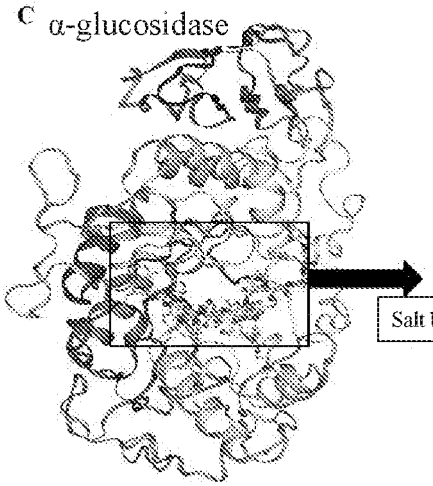
Figure 2D:
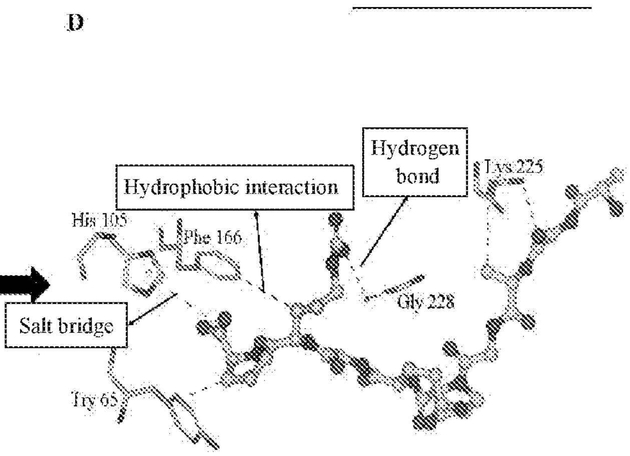
Figure 3A:
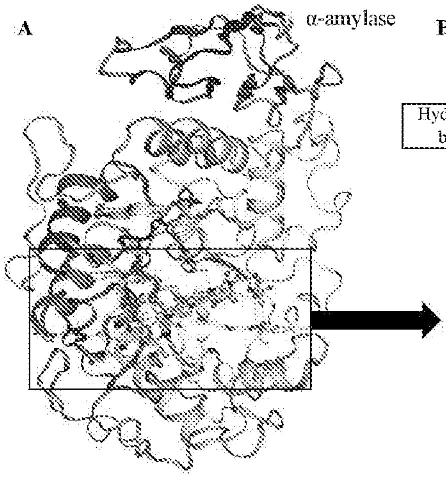
FIGS. 3A-3D show the docking result of FALQGAAFLGSA shown in SEQ ID NO: 3, with α-glucosidase and the docking result of SEQ ID NO: 3 with α-amylase.
Figure 3B:
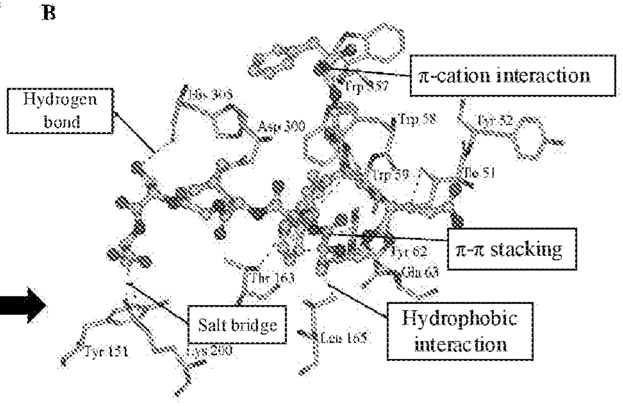
Figure 3C:
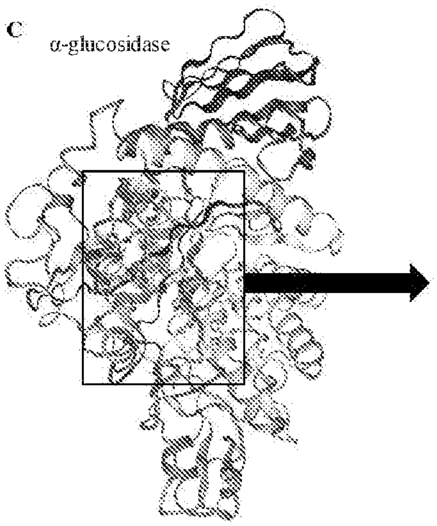
Figure 3D:
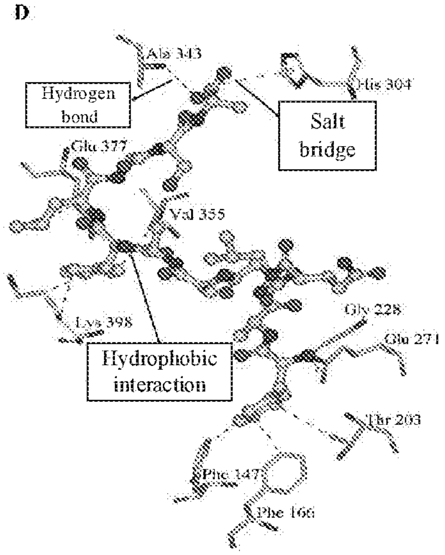
Figure 4A:
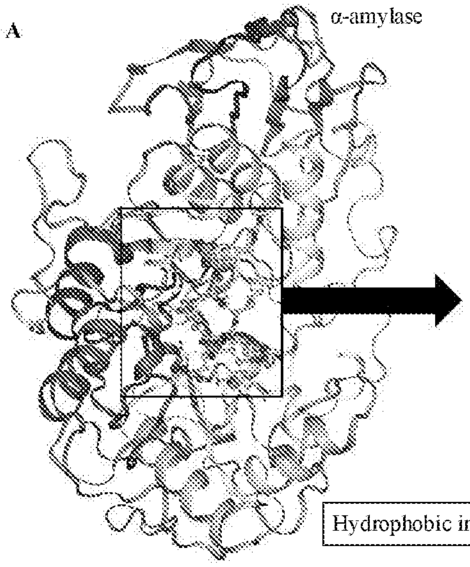
FIGS. 4A-4D show the docking result of QQQQLLR, shown in SEQ ID N with α-glucosidase and the docking result of SEQ ID NO: 4 with α-amylase.
Figure 4B:
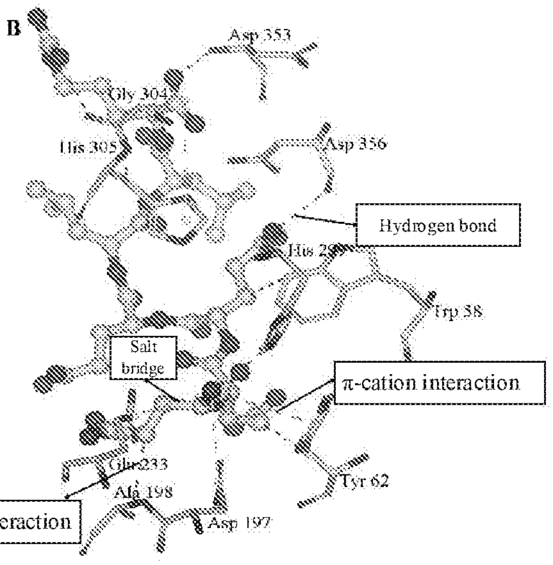
Figure 4C:
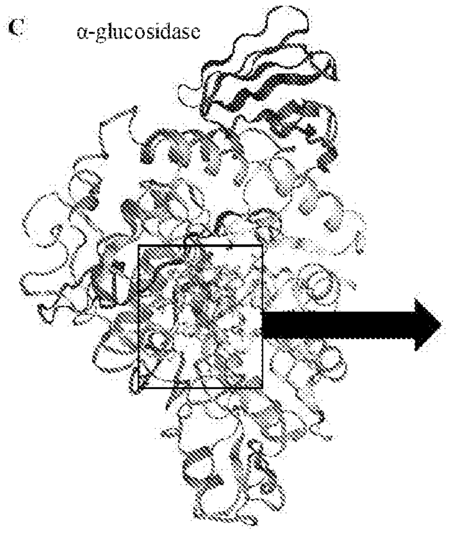
Figure 4D:
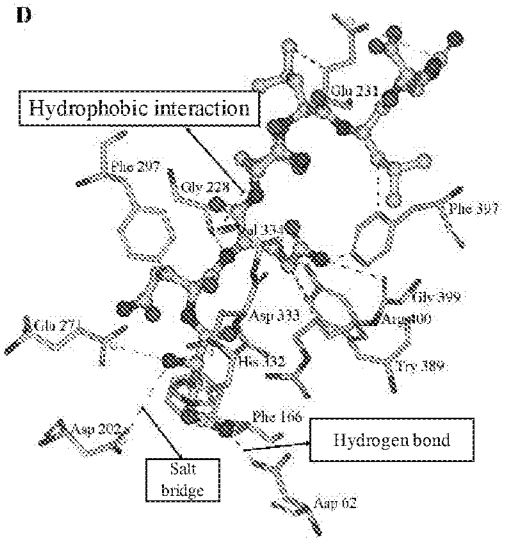
Figure 6A:
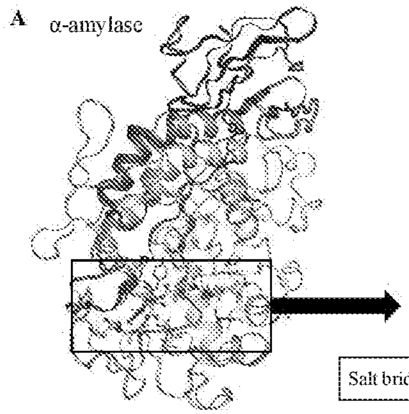
FIGS. 6A-6D show the docking result of KAHAALGAK, shown in SEQ ID NO: 6, with α-glucosidase and the docking result of SEQ ID NO: 6 with α-amylase.
Figure 6B:
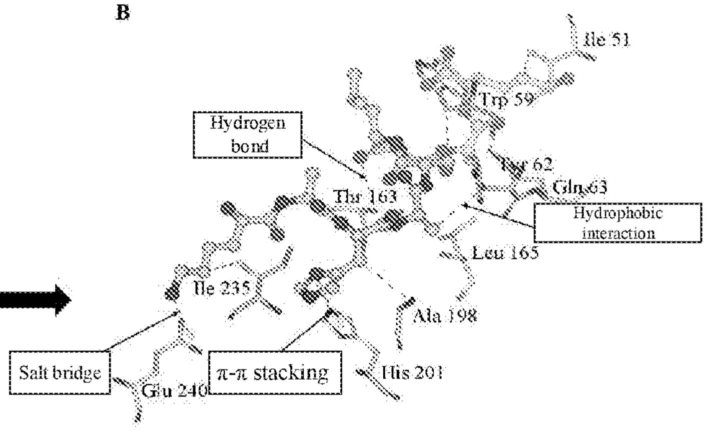
Figure 6C:
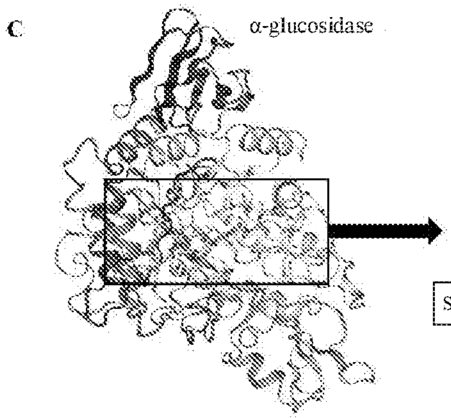
Figure 6D:
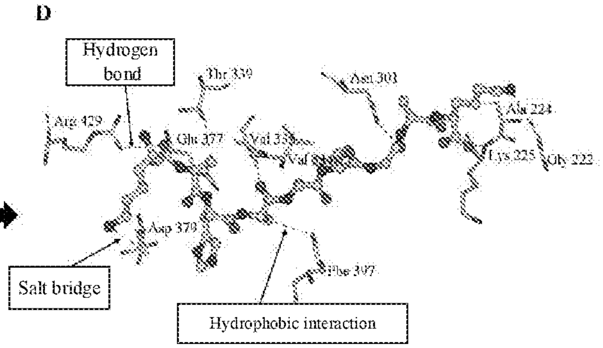

Embodiment 5: Molecular Docking and In Vitro Function Prediction of Hypoglycemic Peptides Screened from Millet Prolamin Precise molecular docking analysis was further conducted using Dock 6.9 software to identify the active sites of QQLRPF shown in SEQ ID NO: 1, AGAGPQGRP shown in SEQ ID NO: 2. FALQGAAFLGSA shown in SEQ ID NO: 3, QQQQLLR shown in SEQ ID NO: 4, KTGSGAEGMHGGK shown in SEQ ID NO: 5, and KAHAALGAK shown in SEQ ID NO: 6 interacted with α-glucosidase and α-amylase. As shown from FIG. 1A to FIG. 1B, the interaction between SEQ ID NO: 1 and α-amylase was analyzed and it was found that SEQ ID NO: 1 forms hydrophobic interactions with residues Trp 59, Leu 165, Trp 58, Try 62, Ile 235, and His 305 of α-amylase, forms hydrogen bonds with residues His 305 and Gin 63 of α-amylase, and forms salt bridges, i.e., ionic bonds, with residues Glu 233 and His 101 of α-amylase. The interaction between-SEQ ID NO: 1 and α-glucosidase was analyzed and it was found that SEQ ID NO: 1 forms hydrophobic interactions with residues Trp 481, Ala 555, Trp 516, Trp 376, Leu 677, Leu 678, Leu 650, Phe 297, Val 334, Ala 343, and Thr 339 of α-glucosidase, forms hydrogen bonds with Thr 339, Arg 429. Gln 427, Gly 399, Asn 301, Gly 651, and Ser 676 of α-glucosidase, forms salt bridges with Asp 282, Asp 616, and Glu 377 of α-glucosidase, and forms π-π stacking with Phe 649 of α-glucosidase (from FIG. 1C to FIG. 1D). As shown from FIG. 2A to FIG. 2B, SEQ ID NO: 2 forms salt bridges with residues Arg 195, His 299, and Asp 356 of α-amylase, and forms hydrogen bonds with residues Leu 237, Glu 233, and His 201 of α-amylase, and forms hydrophobic interactions with Tyr 62, Trp 58, Ile 235, and Leu 165 of α-amylase. In addition, SEQ ID NO: 2 forms a salt bridge with residue His 105 of α-glucosidase, forms hydrophobic interactions with Tyr 65 and Phe 166 of α-glucosidase, and forms hydrogen bonds with Lys 225 and Gly 228 (from FIG. 2C to FIG. 2D). As shown from FIG. 3A to FIG. 3B, SEQ ID NO: 3 forms hydrophobic interactions with residues Tyr 151, Leu 165, Tyr 62, Trp 58, Trp 59, and Ile 51 of α-amylase, forms a salt bridge with Lys 200 of α-amylase, forms hydrogen bonds with His 305, Asp 300, Thr 163. Tyr 52, and Gln 63 of α-amylase, forms π-cation interaction with Trp 357 of α-amylase, and forms π-π stacking with Tyr 62 of α-amylase. Analysis of the interaction between SEQ ID NO: 3 and α-glucosidase reveals that SEQ ID NO: 3 forms hydrophobic interactions with residues Thr 203, Phe 166, Phe 147, Lys 398, Val 335, and Glu 377 of α-glucosidase, forms salt bridges with Glu 271 and His 304 of α-glucosidase, and forms hydrogen bonds with Gly 228 and Ala 348 of α-glucosidase (from FIG. 3C to FIG. 3D). As shown from FIG. 4A to FIG. 4B, SEQ ID NO: 4 forms hydrogen bonds with residues Asp 353, Asp 356, Gly 304, His 299, and Glu 233 of α-amylase, forms salt bridges with His 305, Asp 197, and Glu 233 of α-amylase, forms hydrophobic interactions with His 305, Ala 198, Trp 58, and Tyr 62 of α-amylase, and forms R-cation interaction with Tyr 62 of α-amylase. In addition, SEQ ID NO: 4 forms hydrogen bonds with residues Asp 62, Gly 228, His 332, and Gly 399 of α-glucosidase, forms salt bridges with Asp 202, Asp 333, and Glu 271 of α-glucosidase, and forms hydrophobic interactions with Phe 166, Tyr 389, Arg 400, Val 334, Phe 297, Phe 397, and Glu 231 of α-glucosidase (from FIG. 4C to FIG. 4D), Next, the binding force between α-amylase and peptide fragment SEQ ID NO: 5 was first analyzed, as shown from FIG. 5A to FIG. 5B. Peptide fragment SEQ ID NO: 5 forms hydrophobic interactions with residues Trp 284 and Tyr62 of α-amylase. In addition, residues Lys 200, Lys 225, Lys 261, and Gly 283 of α-amylase are all linked to SEQ ID NO: 5 through hydrogen bonds. In addition to the hydrophobic interactions and hydrogen bonds, π-π stacking is formed between residue His 201 of α-amylase and peptide fragment SEQ ID NO: 5, while residue Trp284 of α-amylase is linked to peptide fragment SEQ ID NO: 5 by π-cation interaction. In addition, His 101, Glu 233, and Glu 272 of α-amylase form salt bridges, i.e., ionic bonds, with peptide fragment SEQ ID NO: 5. As shown from FIG. 5C to FIG. 5D, SEQ ID NO: 5 forms hydrophobic interactions with residues Trp 237 and Lys 221 of α-glucosidase. In addition, residues Gly 399, Lys 225, and Ala 343 of α-glucosidase are all linked to SEQ ID NO: 5 through hydrogen bonds. In addition to hydrophobic interactions and hydrogen bonds, peptide fragment SEQ ID NO: 5 forms a salt bridge, i.e., ionic bond, with residue Arg 429 of α-glucosidase. Finally, the interaction between peptide fragment SEQ ID NO: 6 and α-amylase was analyzed, as shown from FIG. 6A to FIG. 6B. Peptide fragment SEQ ID NO: 6 forms hydrophobic interactions with residues Leu 235, Ala 198, Leu 165, Tyr 62, Ile 51, and. Trp 59 of α-amylase, and forms two hydrogen bonds with residues Gin 63 and Thr 163 of α-amylase, forms a salt bridge (i.e., ionic bond) with residue Glu 240 of α-amylase, and is linked to residue His 201 of α-amylase by π-π stacking interaction. Then, the interaction between peptide fragment SEQ ID NO: 6 and α-glucosidase was analyzed, as shown from FIG. 6C to FIG. 6D, SEQ ID NO: 6 forms hydrophobic interactions with residues Glu 377, Thr 339, Val 334, Val 335, Phe 397, and Ala 224 of α-glucosidase, forms four hydrogen bonds with residues Arg 429, Asn 301, Lys 225, and Gly 222 of α-glucosidase, and forms a salt bridge with residue Asp 379 of α-glucosidase. The stability of SEQ ID NO: 1, SEQ ID NO: 2, SEQ ID NO: 3, SEQ ID NO: 4, SEQ ID NO: 5, and SEQ ID NO: 6 was evaluated through EXPASY platform. The ADMET properties of SEQ ID NO: 1, SEQ ID NO: 2, SEQ ID NO: 3, SEQ ID NO: 4, SEQ ID NO: 5, and SEQ ID NO: 6 were predicted through admetSAR, mainly including human intestinal absorption (HIA) and acute oral toxicity. The results are shown in Table 3 and reveal that the six small peptides have low toxicity, and the three peptides of SEQ ID NO: 5, SEQ ID NO: 6 and SEQ ID NO: 3 have good in vitro stability, while the three peptides of SEQ ID NO: 1, SEQ ID NO: 5 and SEQ ID NO: 6 have good WA properties. In addition, except for SEQ ID NO: 3 being hydrophobic and acidic, SEQ ID NO: 1, SEQ ID NO: 2, SEQ ID NO: 4, SEQ ID NO: 5, and SEQ ID NO: 6 are hydrophilic and alkaline, and SEQ ID NO: 2 has a long half-life period.

dinitrosalicylic acid (DNS) reagent. Then, the resulting solution was boiled in a boiling water bath for 5 min, followed by stopping the reaction and cooling to room temperature. The reaction solution was diluted with 10 mL of distilled water and readed at 540 nm. For the control, deionized water was used to replace the sample. The calculation formula is as follows:

$$\alpha - \text{amylase inhibition rate } (\%) = \frac{A \text{ control} - A \text{ sample}}{A \text{ control}} \times 100\%$$

The method for determining α-glucosidase activity is as follows: First, the solution of substrate 4-Nitrophenyl β-D-glucopyranoside (PNPG) with a concentration of 1.505 mg/mL (5 mmol/L of PNPG dissolved in 0.1 mol/L phosphate buffer with a pH of 6.8) was prepared, a $Na_2CO_3$ solution with a concentration of 0.2 mol/L was prepared, and α-glucosidase solution (0.8 U/ml of α-glucosidase dissolved in 0.1 mol/L phosphate buffer with a pH of 6.8) was prepared. After the solutions were prepared, the following two groups were set for determination:

| Add amount (μL) | Sample group (0.5%) | Control group |
|---|---|---|
| Phosphate buffer | 50 | 70 |
| Sample | 20 | — |
| PNPG solution | 20 | 20 |

After preparing according to the above table, the resulting solution was shaken in a water bath at 37° C. for 10 min, followed by adding 100 μL of enzyme solution and continuing to shake in the water bath at 37° C. for 10 min. Finally, 50 μL of $Na_2CO_3$ solution was added, and the absorbance was measured at 405 nm. The formula for calculating the α-glucosidase inhibition rate is as follows:

$$\alpha - \text{glucosidase inhibition rate} = \frac{A \text{ control} - A \text{ sample}}{A \text{ control}} \times 100\%$$

Figure 7:
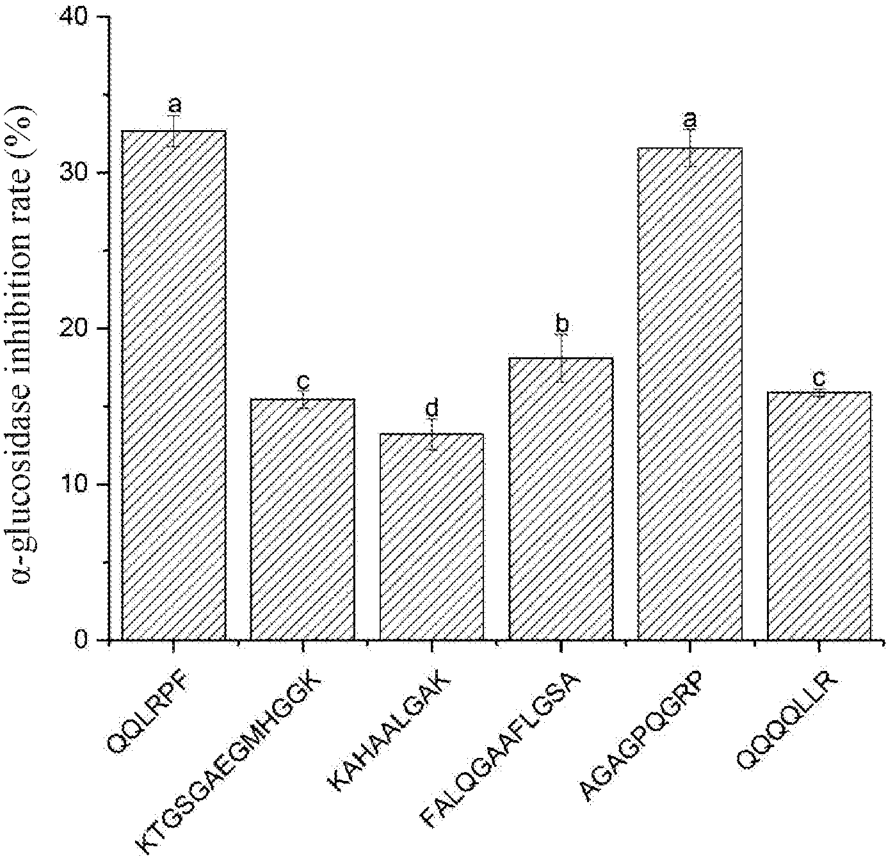
FIG. 7 shows the inhibition rates of QQLRPF shown in SEQ ID NO: 1, AGAGPQGRP shown in SEQ ID NO: 2. FALQGAAFLGSA shown in SEQ ID NO: 3, QQQQLLR shown in SEQ ID NO: 4, KTGSGAEGMHGGK shown in SEQ ID NO: 5, and KAHAALGAK shown in SEQ ID NO: 6 for α-glucosidase.

The results are shown in FIG. 7 and it can be seen that the α-glucosidase inhibition rates of QQLRPF shown in SEQ ID NO: 1 and AGAGPQGRP shown in SEQ ID NO: 2 are

TABLE 3

In vitro function prediction analysis of the peptide fragments of QQLRPF shown in SEQ ID NO: 1, AGAGPQGRP SEQ ID NO: 2, FALQGAAFLGSA SEQ ID NO: 3, QQQQLLR SEQ ID NO: 4, KTGSGAEGMHGGK SEQ ID NO: 5, and KAHAALGAK SEQ ID NO: 6

| SEQ ID NO: | Peptide sequence | Molecular weight (Da) | HIA | In vitro stability | toxicity | hydrophilicity/ hydrophobicity | Theoretical isoelectric point | Half-life period (hour) |
|---|---|---|---|---|---|---|---|---|
| 1 | QQLRPF | 787.92 | + | 136.73 | III | −1.083 | 9.75 | 0.8 |
| 5 | KTGSGAEGMHG GK | 1216.33 | + | 35.22 | III | −1.1 | 8.6 | 1.3 |
| 6 | KAHAALGAK | 866.03 | + | −9.98 | III | −0.04 | 10 | 1.3 |
| 3 | FALQGAAFLGSA | 1152.32 | − | 29.26 | III | 1.275 | 5.52 | 1.1 |
| 2 | AGAGPQGRP | 809.88 | − | 42.26 | III | −0.978 | 9.79 | 4.4 |
| 4 | QQQQLLR | 913.04 | − | 118.63 | III | −1.557 | 9.75 | 0.8 |

Figure 8:
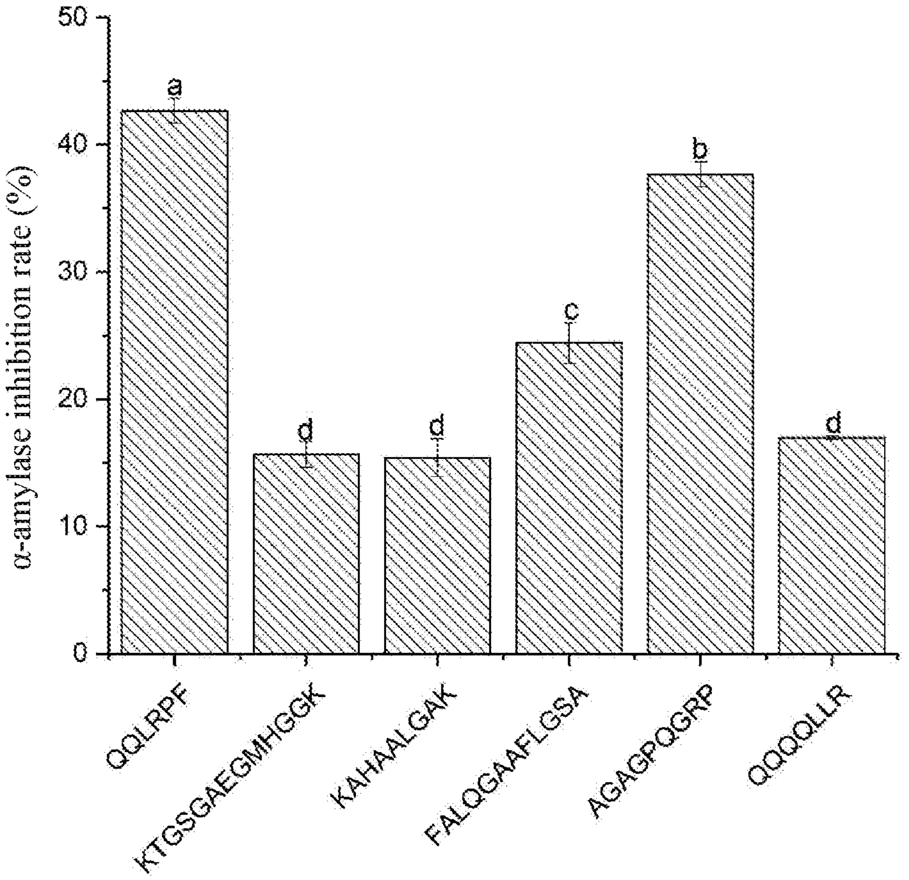
FIG. 8 shows the inhibition rates of QQLRPF shown in SEQ ID NO: 1, AGAGPQGRP shown in SEQ ID NO: 2, FALQGAAFLGSA shown in SEQ ID NO: 3, QQQQLLR shown in SEQ ID NO: 4, KTGSGAEGMHGGK shown in SEQ ID NO: 5, and KAHAALGAK shown in SEQ ID NO: 6 for α-amylase.

Embodiment 6: Determination of In Vitro α-Amylase and α-Glucosidase Inhibitory Activity of Peptide Fragments Screened from Millet Prolamin The method for determining α-amylase activity is as follows: 500 μL of sample (0.5%) and 500 μL of 0.02 mol/L sodium phosphate buffer (pH=6.9, 0.006 mol/L NaCl, and including α-amylase solution (13 U/mL)) were incubated at 25° C. for 10 min. After the pre-incubation, 500 μL of 1% soluble starch solution (0.02 mol/L sodium phosphate buffer, pH=6.9, and 0.006 mol/L NaCl) was added, followed by incubation at 25° C. for 10 min and adding 1.0 mL of 32.67% and 31.57%, respectively, which are significantly higher than those of KTGSGAEGMHGGK shown in SEQ ID NO: 5, KAHAALGAK shown in SEQ ID NO: 6, FALQGAAFLGSA shown in SEQ ID NO: 3, and QQQQLLR shown in SEQ ID NO: 4. The α-glucosidase inhibition rate of SEQ ID NO: 3 is 17.67%, which is significantly higher than those of SEQ ID NO: 5 (15.64%), SEQ ID NO: 6 (13.77%), and SEQ ID NO: 4 (15.94%), while SEQ ID NO: 6 has the lowest oi-glucosidase inhibition rate. As shown in FIG. 8, the α-amylase inhibition rate of SEQ ID NO: 1 is 42.67%, which is the highest and followed by SEQ ID NO: 2 (37.67%), SEQ ID NO: 3 (24.42%), SEQ ID NO: 5 (15.66%), SEQ ID NO. 6 (15.42%), and SEQ ID NO: 4 (16.99%).

SEQUENCE LISTING

```
Sequence total quantity: 26
SEQ ID NO: 1            moltype = AA  length = 6
FEATURE                 Location/Qualifiers
REGION                  1..6
                        note = The sequence is synthetized
source                  1..6
                        mol_type = protein
                        organism = synthetic construct
SEQUENCE: 1
QQLRPF                                                            6

SEQ ID NO: 2            moltype = AA  length = 9
FEATURE                 Location/Qualifiers
REGION                  1..9
                        note = The sequence is synthetized
source                  1..9
                        mol_type = protein
                        organism = synthetic construct
SEQUENCE: 2
AGAGPQGRP                                                         9

SEQ ID NO: 3            moltype = AA  length = 12
FEATURE                 Location/Qualifiers
REGION                  1..12
                        note = The sequence is synthetized
source                  1..12
                        mol_type = protein
                        organism = synthetic construct
SEQUENCE: 3
FALQGAAFLG SA                                                     12

SEQ ID NO: 4            moltype = AA  length = 7
FEATURE                 Location/Qualifiers
REGION                  1..7
                        note = The sequence is synthetized
source                  1..7
                        mol_type = protein
                        organism = synthetic construct
SEQUENCE: 4
QQQQLLR                                                           7

SEQ ID NO: 5            moltype = AA  length = 13
FEATURE                 Location/Qualifiers
REGION                  1..13
                        note = The sequence is synthetized
source                  1..13
                        mol_type = protein
                        organism = synthetic construct
SEQUENCE: 5
KTGSGAEGMH GGK                                                    13

SEQ ID NO: 6            moltype = AA  length = 9
FEATURE                 Location/Qualifiers
REGION                  1..9
                        note = The sequence is synthetized
source                  1..9
                        mol_type = protein
                        organism = synthetic construct
SEQUENCE: 6
KAHAALGAK                                                         9

SEQ ID NO: 7            moltype = AA  length = 12
FEATURE                 Location/Qualifiers
REGION                  1..12
                        note = The sequence is synthetized
source                  1..12
                        mol_type = protein
                        organism = synthetic construct
```

-continued

```
SEQUENCE: 7
TLFDGHAALG AK                                                12

SEQ ID NO: 8           moltype = AA  length = 14
FEATURE                Location/Qualifiers
REGION                 1..14
                       note = The sequence is synthetized
source                 1..14
                       mol_type = protein
                       organism = synthetic construct
SEQUENCE: 8
TSGAAGNGVD AFGQ                                              14

SEQ ID NO: 9           moltype = AA  length = 7
FEATURE                Location/Qualifiers
REGION                 1..7
                       note = The sequence is synthetized
source                 1..7
                       mol_type = protein
                       organism = synthetic construct
SEQUENCE: 9
THVKKQQ                                                      7

SEQ ID NO: 10          moltype = AA  length = 6
FEATURE                Location/Qualifiers
REGION                 1..6
                       note = The sequence is synthetized
source                 1..6
                       mol_type = protein
                       organism = synthetic construct
SEQUENCE: 10
FQQFRP                                                       6

SEQ ID NO: 11          moltype = AA  length = 7
FEATURE                Location/Qualifiers
REGION                 1..7
                       note = The sequence is synthetized
source                 1..7
                       mol_type = protein
                       organism = synthetic construct
SEQUENCE: 11
QQLLLPW                                                      7

SEQ ID NO: 12          moltype = AA  length = 9
FEATURE                Location/Qualifiers
REGION                 1..9
                       note = The sequence is synthetized
source                 1..9
                       mol_type = protein
                       organism = synthetic construct
SEQUENCE: 12
GPAGHVKNQ                                                    9

SEQ ID NO: 13          moltype = AA  length = 8
FEATURE                Location/Qualifiers
REGION                 1..8
                       note = The sequence is synthetized
source                 1..8
                       mol_type = protein
                       organism = synthetic construct
SEQUENCE: 13
TMAALGAK                                                     8

SEQ ID NO: 14          moltype = AA  length = 9
FEATURE                Location/Qualifiers
REGION                 1..9
                       note = The sequence is synthetized
source                 1..9
                       mol_type = protein
                       organism = synthetic construct
SEQUENCE: 14
QGGPAGGRP                                                    9

SEQ ID NO: 15          moltype = AA  length = 9
FEATURE                Location/Qualifiers
REGION                 1..9
                       note = The sequence is synthetized
source                 1..9
                       mol_type = protein
```

-continued

```
                        organism = synthetic construct
SEQUENCE: 15
GPAGPQGPR                                                                  9

SEQ ID NO: 16           moltype = AA  length = 8
FEATURE                 Location/Qualifiers
REGION                  1..8
                        note = The sequence is synthetized
source                  1..8
                        mol_type = protein
                        organism = synthetic construct
SEQUENCE: 16
PSLVRGPR                                                                   8

SEQ ID NO: 17           moltype = AA  length = 7
FEATURE                 Location/Qualifiers
REGION                  1..7
                        note = The sequence is synthetized
source                  1..7
                        mol_type = protein
                        organism = synthetic construct
SEQUENCE: 17
AGPAGRP                                                                    7

SEQ ID NO: 18           moltype = AA  length = 6
FEATURE                 Location/Qualifiers
REGION                  1..6
                        note = The sequence is synthetized
source                  1..6
                        mol_type = protein
                        organism = synthetic construct
SEQUENCE: 18
TNRFKP                                                                     6

SEQ ID NO: 19           moltype = AA  length = 7
FEATURE                 Location/Qualifiers
REGION                  1..7
                        note = The sequence is synthetized
source                  1..7
                        mol_type = protein
                        organism = synthetic construct
SEQUENCE: 19
QQLLAPW                                                                    7

SEQ ID NO: 20           moltype = AA  length = 7
FEATURE                 Location/Qualifiers
REGION                  1..7
                        note = The sequence is synthetized
source                  1..7
                        mol_type = protein
                        organism = synthetic construct
SEQUENCE: 20
FTSSKPF                                                                    7

SEQ ID NO: 21           moltype = AA  length = 8
FEATURE                 Location/Qualifiers
REGION                  1..8
                        note = The sequence is synthetized
source                  1..8
                        mol_type = protein
                        organism = synthetic construct
SEQUENCE: 21
THEGQMSP                                                                   8

SEQ ID NO: 22           moltype = AA  length = 6
FEATURE                 Location/Qualifiers
REGION                  1..6
                        note = The sequence is synthetized
source                  1..6
                        mol_type = protein
                        organism = synthetic construct
SEQUENCE: 22
FSWTPR                                                                     6

SEQ ID NO: 23           moltype = AA  length = 8
FEATURE                 Location/Qualifiers
REGION                  1..8
                        note = The sequence is synthetized
source                  1..8
```

-continued

```
                        mol_type = protein
                        organism = synthetic construct
SEQUENCE: 23
YGVTHPCG                                                     8

SEQ ID NO: 24           moltype = AA  length = 6
FEATURE                 Location/Qualifiers
REGION                  1..6
                        note = The sequence is synthetized
source                  1..6
                        mol_type = protein
                        organism = synthetic construct
SEQUENCE: 24
YAMTPR                                                       6

SEQ ID NO: 25           moltype = AA  length = 6
FEATURE                 Location/Qualifiers
REGION                  1..6
                        note = The sequence is synthetized
source                  1..6
                        mol_type = protein
                        organism = synthetic construct
SEQUENCE: 25
FYWTPR                                                       6

SEQ ID NO: 26           moltype = AA  length = 6
FEATURE                 Location/Qualifiers
REGION                  1..6
                        note = The sequence is synthetized
source                  1..6
                        mol_type = protein
                        organism = synthetic construct
SEQUENCE: 26
QQFYPF                                                       6
```

What is claimed is:

1. A method for preparing hypoglycemic drugs, food products, or health products suitable for a diabetic population comprising the step of adding a cooked millet prolamin peptide hydrolysate for inhibiting an α-amylase and an α-glucosidase to an acceptable excipient for a pharmaceutical product, food product, or health product, wherein the cooked millet prolamin peptide hydrolysate is a hydrolysate of enzyme-digested millet protein, wherein the millet protein peptide hydrolysate comprises small peptides comprising sequences selected from the group consisting of SEQ ID NO: 1, SEQ ID NO: 2, SEQ ID NO: 3, SEQ ID NO: 4, SEQ ID ND: 5, and SEQ ID NO: 6.

2. The method according to claim 1, wherein the pharmaceutical product, food product, or health product is for treating type 2 diabetes.

3. The method according to claim 1, wherein the millet prolamin peptide hydrolysate small peptides comprise sequences selected from the group consisting of SEQ ID NO: 1 and SEQ ID NO: 2.

* * * * *